United States Patent [19]

Masaki

[11] 4,198,939
[45] Apr. 22, 1980

[54] METHOD OF CONTROLLING THE AIR-FUEL RATIO OF AN ENGINE AIR-FUEL MIXTURE AND A SYSTEM FOR EXECUTING THE METHOD

[75] Inventor: Kenji Masaki, Yokohama, Japan

[73] Assignee: Nissan Motor Company, Limited, Japan

[21] Appl. No.: 840,099

[22] Filed: Oct. 6, 1977

[30] Foreign Application Priority Data

Oct. 8, 1976 [JP] Japan .................... 51-121407

[51] Int. Cl.² .......................................... F02B 3/00
[52] U.S. Cl. ............................ 123/119 EC; 60/276; 60/285
[58] Field of Search ............. 123/119 EC, 139 AW, 123/119 E; 60/276, 285, 119 W, 278, 285; 204/195 S

[56] References Cited

U.S. PATENT DOCUMENTS

| | | | |
|---|---|---|---|
| 3,546,086 | 10/1970 | Sayles | 204/195 S |
| 3,558,280 | 1/1971 | Panson et al. | 204/195 S |
| 3,616,274 | 10/1971 | Eddy | 204/195 S |
| 3,723,279 | 3/1973 | Freehan et al. | 204/195 S |
| 3,847,778 | 11/1974 | Riddel | 60/285 |
| 3,949,551 | 4/1976 | Eichler et al. | 60/276 |
| 4,005,689 | 2/1977 | Barnard | 60/278 |
| 4,023,357 | 5/1977 | Masaki | 60/285 |
| 4,023,359 | 5/1977 | Masaki et al. | 60/28 J |
| 4,050,425 | 9/1977 | Holleboom | 123/119 EC |
| 4,076,608 | 2/1978 | Fujishiro et al. | 204/195 S |
| 4,080,276 | 3/1978 | Bode | 60/276 |
| 4,103,649 | 8/1978 | Matumoto et al. | 123/119 EC |
| 4,108,122 | 8/1978 | Barnard | 60/276 |

Primary Examiner—Ronald H. Lazarus
Assistant Examiner—R. A. Nelli
Attorney, Agent, or Firm—Lowe, King, Price & Becker

[57] ABSTRACT

A sensor is located in the intake passageway of an engine for sensing a parameter representing a function of the air-fuel ratio of an air-fuel mixture produced for the engine and is heated to a predetermined temperature when the temperature of the sensor is below the predetermined temperature above which it is possible for the sensor to sense the parameter.

8 Claims, 2 Drawing Figures

METHOD OF CONTROLLING THE AIR-FUEL RATIO OF AN ENGINE AIR-FUEL MIXTURE AND A SYSTEM FOR EXECUTING THE METHOD

BACKGROUND OF THE INVENTION

1. Field of the Invention

The present invention relates generally to a method of and a system for controlling the air-fuel ratio of an air-fuel mixture produced for an internal combustion engine to a desired air-fuel ratio and particularly to a method and a system of this type in which the time required from provision of the air-fuel mixture to detection of a parameter representative of a function of the air-fuel ratio of the air-fuel mixture is reduced.

2. Description of the Prior Art

As is well known in the art, in a conventional air-fuel ratio control system, the air-fuel ratio of an air-fuel mixture produced for the engine has been controlled to a desired air-fuel ratio in accordance with a parameter representing an air-fuel ratio which has been sensed by a sensor located in the exhaust system of the engine.

Thus, the conventional air-fuel ratio control system has had a drawback that since an undesirably long time is required from production of an engine air-fuel mixture to detection of the air-fuel ratio of the air-fuel mixture due to the sensor being provided in the exhaust system, it is impossible to effectively control the air-fuel ratio of an engine air-fuel mixture to a desired air-fuel ratio.

As a solution to this problem, an air-fuel ratio control system has been proposed in which a part of an air-fuel mixture produced for an engine is extracted from the intake passageway thereof into a combustion gas generator, the extracted air-fuel mixture is burned in the combustion gas generator to form combustion gases therein, a sensor senses a parameter representative of a function of the concentration of a specific component in the combustion gases which concentration is closely related to the air-fuel ratio of the extracted air-fuel mixture, and the air-fuel ratio of an air-fuel mixture produced for the engine is controlled to a desired air-fuel ratio in accordance with the sensed parameter.

However, in this conventional air-fuel ratio control system, exhaust gases resulting from the combustion gases are conducted into the exhaust gas passageway of the engine. As a result, the conventional system requires measures for maintaining the pressure of the combustion gases at a tolerably high level. This is to make combustion of the extracted air-fuel mixture possible in spite of a high back pressure in the exhaust gas passageway and to at all times maintain stable combustion of the extracted air-fuel mixture without being influenced by variations in the pressure of engine exhaust gases in the exhaust gas passageway due to variations in engine load. Furthermore, when the extracted air-fuel mixture is not burned in the combustion gas generator due to a malfunction, or the like, the unburned air-fuel mixture is discharged to the atmosphere through the exhaust gas passageway to contaminate the atmosphere and at times the unburned air-fuel mixture causes an extraordinary combustion in the exhaust gas passageway to make the engine dangerous.

SUMMARY OF THE INVENTION

It is, therefore, an object of the invention to provide a method of and a system for controlling the air-fuel ratio of an air-fuel mixture produced for an engine which system fails to require the above-mentioned measures and to exert bad influences as mentioned above on the engine and on the atmosphere and which are free from a problem in safety.

This object is accomplished by providing the above-mentioned sensor in the intake passageway of the engine adjacent to a portion at which the air-fuel mixture is produced.

BRIEF DESCRIPTION OF THE DRAWINGS

This and other features and advantages of the invention will become more apparent from the following detailed description taken in connection with the accompanying drawings in which.

DESCRIPTION OF THE PREFERRED EMBODIMENT

Figure 1:
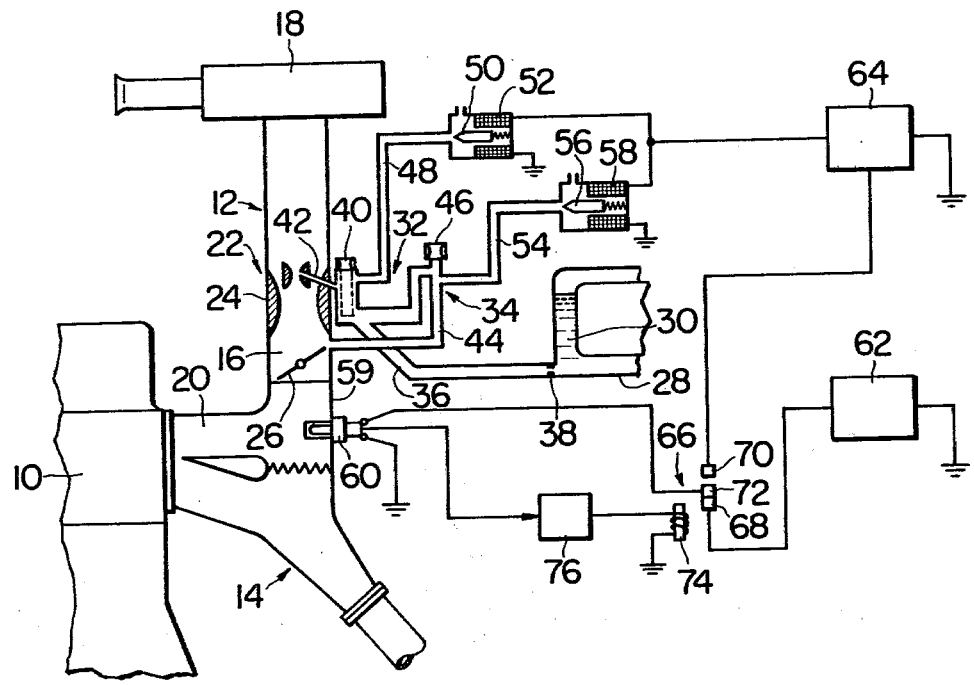
FIG. 1 is a schematic view of a preferred embodiment of an air-fuel ratio control system according to the invention.

Referring to FIG. 1 of the drawings, there is shown an air-fuel ratio control system according to the invention which is combined with an internal combustion engine. The engine 10 is equipped with intake and exhaust systems 12 and 14. The intake system 12 includes an intake passageway or conduit 16 providing communication between the atmosphere and the engine 10 through an air cleaner 18 for conducting atmospheric air into the engine 10. An intake manifold 20 is fixedly secured to the engine 10 to form a part of the intake passageway 16. A carburetor 22 is fixedly secured to the intake manifold 20 to include a part of the intake passageway 16. The carburetor 22 has a venturi 24 formed in the intake passageway 16, and a throttle valve 26 rotatably mounted in the intake passageway 16 downstream of the venturi 24. The carburetor 22 also has a float chamber 28 containing liquid fuel 30 therein, a main system 32 and a slow speed system 34. The main system 32 includes a main fuel passage 36 communicating with the float chamber 28 through a main jet 28, a main air bleed passage 40 communicating with the atmosphere and with the main fuel passage 36, and a main nozzle 42 commnicating with the main fuel passage 36 and opening into the venturi 24. The slow speed system 34 includes a slow speed fuel passage 44 communicating with the main fuel passage 36 downstream of the main jet 38, and a slow speed air bleed passage 46 communicating with the atmosphere and with the slow speed fuel passage 44.

The air-fuel ratio control system comprises a fuel flow control device comprising an additional main air bleed passage 48 communicating with the atmosphere and with the main air bleed passage 40, an electromagnetically operated valve 50 for controlling the additional main air bleed passage 48 and which has a solenoid coil 52 for operating same, an additional slow speed air bleed passage 54 communicating with the atmosphere and with the slow speed air bleed passage 46, and an electromagnetically operated valve 56 for controlling the additional slow speed air bleed passage 52 and which has a solenoid coil 58 for operating same. A sensor 60 is located in the intake passageway 16 for sensing the concentration of a specific component of an air-fuel mixture produced therein by the carburetor 22 which concentration is closely related to the air-fuel ratio of the air-fuel mixture. The sensor 60 senses the concentration of the specific component by sensing a parameter such as, for example, the partial pressure of the specific component which represents a function of the concentration of the specific component. Although the sensor 60 is attached to a riser portion 59 of the intake passageway 16 as shown in the drawing in this embodiment, the sensor 60 may be attached to the intake passageway 16 at a portion such as, for example, a specific branch portion of the intake manifold 20 at which portion air and fuel are satisfactorily mixed. The sensor 60 generates an output signal representative of the sensed concentration of the specific component. The sensor 60 is alternatively and electrically connected to an electrical power source 62 and to a control device 64 through a switch-over device 66.

The control device 64 is electrically connected to both the solenoid coils 52 and 58. The control device 66 receives the output signal of the sensor 60 and generates a control or command signal in accordance with the output signal from the sensor 60 which control signal is applied to each of the solenoid coils 52 and 58 to cause same to control the degree of opening of the corresponding control valve 50 or 56 in accordance with the sensed concentration of the specific component. Both the control valves 50 and 56 are operated by the solenoid coils 52 and 58, respectively to increase or reduce the amount of fuel drawn from the main and slow speed fuel passages 36 and 44 into the intake passageway 16 to thereby control the air-fuel ratio of an air-fuel mixture produced by the carburetor to a desired or predetermined air-fuel ratio by reducing or increasing the amount of atmospheric air, drawn into the intake passageway 16 through the additional air bleed passages 48 and 54, in accordance with the control signal from the control device 66.

The switch-over device 66 comprises a first stationary contact 68 connected to the electric power source 62, a second stationary contact 70 connected to the control device 64, a movable contact 72 connected to the sensor 60, and a relay coil 74 for switching over contact or engagement of the movable contact 72 between the first and second stationary contacts 68 and 70. The relay coil 74 is electrically connected through an amplifying and discriminating device 76 to a temperature sensor for sensing the temperature of the sensor 60 and which will be again referred to hereinafter. The temperature sensor generates an output signal representative of the sensed temperature of the sensor 60 which is applied to the device 76. The device 76 compares the value of the output signal of the temperature sensor with a reference or set value and discriminates whether the temperature of the sensor 60 is higher or lower than a set temperature corresponding to the set value. When the temperature of the sensor 60 is lower than the set temperature, the device 76 generates an output signal for energizing or deenergizing the relay coil 74 to cause the movable contact 72 to contact with the first stationary contact 68. As a result, the sensor 60, the contacts 68 and 72 and the electric power source 62 form a heating circuit for heating the sensor 62 to the set temperature at which it is made possible for the sensor 60 to sense the concentration of the specific component. Conversely, when the temperature of the sensor 60 is higher than the set temperature, the device 76 generates an output signal for deenergizing or energizing the relay coil 74 to cause the movable contact 72 to contact with the second stationary contact 70. As a result, the sensor 60, the contacts 70 and 72 and the device 76 form an air-fuel ratio control circuit by which the air-fuel ratio of the air-fuel mixture is controlled to the desired value. When the output signal of the device 76 energizes the relay coil 74, the device 76 serves to increase the amplitude of the output signal thereof above that of the output signal of the temperature sensor for rendering it possible to energize the relay coil 74.

Figure 2:
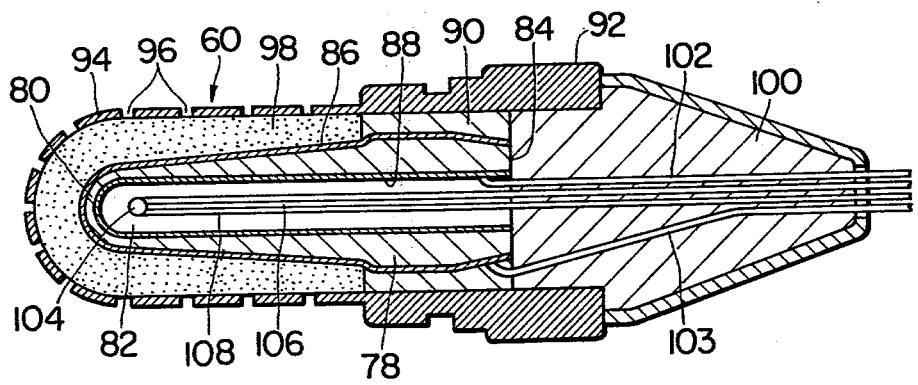
FIG. 2 is a schematic cross sectional view of an example of a sensor employed in the air-fuel ratio control system shown in FIG. 1.

Referring to FIG. 2 of the drawings, there is shown the detail of an example of the sensor 60. As shown in FIG. 2, the sensor 60 comprises an oxygen concentration cell comprising a solid electrolyte 78 such as, for example, zirconium oxide ($ZrO_2$) which is in the shape of a cylinder. The solid electrolyte 78 defines an elongate hollow 82 and has at one annular end thereof a continuous closure portion or extension 80 connected to the entire length of the annular end and closing an end of the elongate hollow portion 82 of the cylinder to form a blind end of the hollow portion 82 and lacks at the other annular end 84 thereof such a closure extension to form an open end of the hollow portion 82. External and internal surfaces of the solid electrolyte 78 are coated respectively with layers 86 and 88 which each are made of, for example, platinum and which serve as or form electrodes. An electric conductor 90 is located on an external surface of the external layer 86 near the annular end 84 of the solid electrolyte 78. The solid electrolyte 78 is fixedly secured to a base or body 92 through the conductor 90 so that it is electrically connected to the base 92. A cover 94 is fixedly secured to the base 92 to surround a portion of the external layer 86 outer than a portion thereof having the conductor 90 and is spaced apart from the external layer 86 so that a space is formed between the external layer 86 and the cover 94. The cover 94 may be made of a metal and is formed therethrough over nearly the entire area thereof with a number of small apertures 96. An electrode protective layer 98 fills the space between the external layer 86 and the cover 94 to surround the solid electrolyte 78. The electrode protective layer 98 may be made of, for example, perforated ceramics. An insulator 100 is provided which occupies a right-hand portion in the drawing of the solid electrolyte 78 so that the base 92 is located between the cover 94 and the insulator 100. The insulator 100 is connected at an end thereof to the annular end 84 of the solid electrolyte 78 and the base 92.

A lead wire 102 extends from the internal layer 88 outside the sensor 60 through the insulator 100 and is connected to the movable contact 72 of the switchover device 66. The external layer 86 is grounded through the conductor 90 and the base 92. Alternatively, the external layer 86 may be grounded through a lead wire 103 extending from the external layer 86 through the insulator 100. The temperature sensor 104 mentioned hereinbefore is located in the hollow portion 82 of the solid electrolyte 78 adjacent to the closure portion 80. Lead wires 106 and 108 extend from the temperature sensor 104 outside the sensor 60 through the insulator 100. One of the lead wires 106 and 108 is connected to the amplifying and discriminating device 76. The other lead wire 106 or 108 is grounded. Alternatively, the lead wire 106 or 108 may be grounded through the base 92 by connecting the lead wire to the base 92.

The hollow portion 82 communicates with the ambient atmosphere through a clearance (not shown) between the insulator 100 and each of the lead wires 102, 106 and 108. An independent passage or small bore (not shown) may be formed through the insulator 100 for independently providing communication between the hollow portion and the atmosphere.

The sensor 60 is fixedly secured to the intake passageway 16 so that the porous cover 94 is located in the intake passageway 16 and is exposed to the flow of the air-fuel mixture passing in the intake passageway 16.

The air-fuel ratio control system thus described is operated in this manner.

When the temperature sensor 104 senses a temperature of the sensor 60 below a predetermined or set value which is usually about 300° C., the device 76 generates an output signal which is applied to the relay coil 66. The relay coil 66 causes the movable contact 72 to contact with the first stationary contact 68 in response to the output signal of the device 76. As a result, since the electric power source 62 is connected to the sensor 60 to pass an electric current through the electrodes 86 and 88 thereof, the electrodes 86 and 88 are heated to increase the temperature of the solid electrolyte 78 above the set value. When the temperature sensor 104 senses a temperature of the sensor 60 increased above the set value, the device 76 generates an output signal which causes the relay coil 66 to switch over engagement of the movable contact 72 from the first stationary contact 68 to the second stationary contact 70. As a result, the sensor 60 is isolated from the electric power source 62 and is connected to the control device 64.

On the other hand, the air-fuel mixture passing in the intake passageway 16 permeates from the apertures 96 of the metal cover 94 through the electrode protective layer 98 to the external electrode 86 and is then oxidized by a catalytic reaction caused by the platinum layer 86 of the heated electrode. As the result of such a reaction, the oxygen concentration cell generates an electromotive force or a voltage in accordance with the difference between the concentration of oxygen in the air-fuel mixture contacting with the external electrode 86 and the concentration of oxygen in atmospheric air contacting with the internal electrode 88. The voltage produced in the oxygen concentration cell is fed to the control device 64. The control device 64 compares the value of the voltage and therefore the sensed concentration of oxygen in the air-fuel mixture produced for the engine 10 with a reference or desired value corresponding to a desired air-fuel ratio of the air-fuel mixture. When the sensed air-fuel ratio is above the desired air-fuel ratio, the control device 64 generates an output signal which causes both the control valves 50 and 56 to reduce the amount of atmospheric air drawn through the air bleed passages 48 and 54, respectively, into the intake passageway 16 to, for example, zero for increasing the amounts of fuel drawn from the main and slow speed fuel passages 36 and 44 into the intake passageway 16 to reduce the air-fuel ratio of an air-fuel mixture produced for the engine 10 to the desired air-fuel ratio. Conversely, when the sensed air-fuel ratio is below the desired air-fuel ratio, the control device 64 generates an output signal which causes both the control valves 50 and 56 to increase the amount of atmospheric air drawn through the air bleed passages 48 and 54, respectively, into the intake passageway 16 for reducing the amounts of fuel drawn from the fuel passages 36 and 44 into the intake passageway 16 to increase the air-fuel ratio of an air-fuel mixture produced for the engine 10 to the desired air-fuel ratio.

Once the temperature of the sensor 60 is increased to the set value to continue to sense the concentration of oxygen in the engine air-fuel mixture, since the external electrode 86 is held at a high temperature due to a catalytic reaction of the air-fuel mixture having an air-fuel ratio equal to or near a stoichiometric air-fuel ratio, it is unnecessary to feed an electric current to the sensor 60 for heating the electrodes 86 and 88.

It is desirable to employ an oxidation catalyst as the electrode preventive layer 98, since the oxidation catalyst is effective for promotion of the catalytic reaction of the air-fuel mixture and maintenance of the temperature of the sensor 60.

Although the invention has been described as being applied to an engine employing a carburetor as an air-fuel mixture producing device, it can be obviously applied to an engine employing a fuel injection device as the air-fuel mixture producing device.

It will be appreciated that the invention provides a method of and a system for controlling the air-fuel ratio of an air-fuel mixture produced for an engine to a desired value in which a sensor for sensing a parameter representing the air-fuel ratio is located in the intake passageway so that the air-fuel ratio of an engine air-fuel mixture is effectively controlled to the desired value due to the time required from production of an engine air-fuel mixture to detection of the air-fuel ratio thereof being reduced without being accompanied by the above-mentioned inconveniences encountered in the last-mentioned conventional air-fuel ratio control system and without being accompanied by inconveniences encountered in a case in which an air-fuel ratio is sensed from a sampling air-fuel mixture different from an engine air-fuel mixture and without being complicated in steps or construction.

It will be also appreciated that the invention provides a method and a system of this type in which the sensor is heated to a predetermined temperature when the temperature of the sensor is below the predetermined value above which it is possible for the sensor to sense the parameter, so that the sensor is able to surely sense the parameter even when the temperature of the engine is below the above-mentioned predetermined value.

What is claimed is:

1. A method of controlling the air-fuel ratio of an air-fuel mixture produced for an internal combustion engine having an intake passageway, a fuel flow control device, an air-fuel ratio sensor of a type that is responsive to air-fuel ratio of a gas mixture only when said sensor is at a temperature higher than a fixed temperature, said fuel flow control device being selectively connected to be responsive to said sensor, and an electrical power source, comprising the steps of using said sensor, sensing a parameter representative of an air-fuel ratio of the air-fuel mixture in said intake prior to any combustion of said mixture;

monitoring a temperature of said sensor;

comparing said monitored temperature with said fixed temperature and generating (1) a first electrical signal when said monitored temperature is higher than said fixed temperature and (2) a second electrical signal when said monitored temperature is below said fixed temperature;

in response to said first electrical signal, electrically connecting said sensor to a first circuit including said power source for energizing an external heating means to heat said sensor and electrically disconnecting said sensor from a second circuit including said fuel flow control device; and in response to said second electrical signal, electrically disconnecting said sensor from said first circuit and electrically connecting said sensor to said second circuit.

2. A method as claimed in claim 1, wherein said sensor comprises an oxygen concentration cell comprising a solid electrolyte and first and second electrodes located respectively on external and internal surfaces of said electrolyte, wherein said steps of controlling said fuel flow control device by said sensor output signal and inhibiting said output signal include respectively connecting and disconnecting said second electrode of said sensor with respect to said fuel flow control device and further wherein said steps of heating and inhibiting heating of said sensor include the steps respectively of connecting and disconnecting said second electrode of said sensor with respect to said electrical power source.

3. In an internal combustion engine having means defining an intake passageway providing communication between the atmosphere and the engine and an air-fuel mixture producing device for producing an air-fuel mixture for the engine in the intake passageway at a predetermined location, an air-fuel ratio control system comprising:

an air-fuel ratio sensor positioned in the intake passageway downstream of said predetermined location for sensing a parameter representative of the air-fuel ratio of only a pre-ignition air-fuel mixture produced in the intake passageway, a fuel flow control device selectively connectable to said air-fuel ratio sensor for controlling the air-fuel ratio of an air-fuel mixture produced by the air-fuel mixture producing device to a desired value by controlling the flow rate of fuel, fed into the intake passageway for production of the air-fuel mixture, in accordance with the sensed parameter only when said air-fuel ratio sensor is connected to said fuel flow control device, electric heating means actuable for heating said air-fuel ratio sensor, a temperature sensor for sensing the temperature of said air-fuel ratio sensor and for generating an output signal representative of the sensed temperature, means for generating a reference temperature electrical signal having a predetermined value, discriminating means electrically connected to said temperature sensor for comparing the value of said output signal thereof with the predetermined value and for generating first and second signals in response to values of said output signals of said temperature sensor which are below and above said predetermined value respectively, and switch-over means electrically connected to said discriminating means for (1) connecting said air-fuel ratio sensor in a first circuit including means for actuating said electric heating means and for disconnecting said sensor from said fuel flow control device in response to said first signal of said discriminating means and for (2) connecting said air-fuel ratio sensor in a second circuit including means for deactuating said electric heating means and for connecting said sensor to said fuel flow control device in response to said second signal of said discriminating means.

4. An air-fuel ratio control system as claimed in claim 3, in which said heating means comprises
an electric power source, and said switch-over means comprises
a first stationary contact connected to said electric power source,
a second stationary contact connected to said fuel flow control device,
a movable contact connected to said air-fuel ratio sensor and contactable alternatively with said first and second stationary contacts, and
a relay coil connected to said discriminating means for causing said movable contact to contact with said first stationary contact in response to said first signal of said discriminating means and for causing said movable contact to contact with said second stationary contact in response to said second signal of said discriminating means.

5. An air-fuel ratio control system as claimed in claim 4, in which said air-fuel ratio sensor comprises
an oxygen concentration cell comprising
a solid electrolyte defining an elongate hollow,
a first electrode made of platinum and located on an external surface of said solid electrolyte, and
a second electrode made of platinum and located on an internal surface of said solid electrolyte and connected to said movable contact;
a base for supporting said solid electrolyte at a position adjacent to an inner end of said elongate hollow;
a porous protective layer surrounding said solid electrolyte; and
a porous cover extending from said base and enclosing said protective layer and located in the intake passageway so that it is exposed to the air-fuel mixture therein.

6. An air-fuel ratio control system as claimed in claim 5, in which said electric heating means comprises
said second electrode, and
a lead wire connecting said second electrode to said movable contact.

7. An air-fuel ratio control system as claimed in claim 5, in which said temperature sensor is located in said elongate hollow of said solid electrolyte.

8. An air-fuel ratio control system as claimed in claim 5, in which said porous protective layer is formed of an oxidation catalyst.

* * * * *